US006667294B2

(12) United States Patent
Jones et al.

(10) Patent No.: US 6,667,294 B2
(45) Date of Patent: *Dec. 23, 2003

(54) MICROENCAPSULATED DNA FOR VACCINATION AND GENE THERAPY

(75) Inventors: David Hugh Jones, Devizes (GB); Graham Henry Farrar, Salisbury (GB); James Christopher Stephen Clegg, Salisbury (GB)

(73) Assignee: Microbiological Research Authority, Salisbury (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/745,515

(22) Filed: Nov. 12, 1996

(65) Prior Publication Data

US 2002/0041867 A1 Apr. 11, 2002

(30) Foreign Application Priority Data

Nov. 9, 1995 (GB) ............................................. 9523019
Jan. 31, 1996 (GB) ............................................. 9601929

(51) Int. Cl.⁷ ......................... A61K 48/00; A61K 9/50; C12N 15/63

(52) U.S. Cl. ...................... 514/44; 424/489; 424/490; 435/320.1; 435/455

(58) Field of Search ............................. 514/44; 933/53, 933/55, 60, 65; 435/325, 69.1, 320.1, 455; 424/408, 412, 428, 482, 489, 490, 93.6

(56) References Cited

U.S. PATENT DOCUMENTS

| 3,523,906 A | 8/1970 | Vrancken et al. ............. 252/316 |
| 4,262,090 A | 4/1981 | Colby, Jr. et al. .............. 435/91 |

(List continued on next page.)

FOREIGN PATENT DOCUMENTS

| CA | 2126685 | 5/1994 | |
| EP | 0 027 662 A1 | 4/1981 | |
| EP | 0127713 | 12/1984 | |
| EP | 0 145 240 A2 | 6/1985 | |
| EP | 0 161 640 | 11/1985 | |
| EP | 0 179 023 A2 | 4/1986 | |
| EP | 0 248 531 | 12/1987 | |
| EP | 0 250 038 A2 | 12/1987 | |
| EP | 0257915 | 3/1988 | ............ A61K/9/50 |
| EP | 0 258 749 A2 | 3/1988 | |
| EP | 0 263 490 A2 | 4/1988 | |
| EP | 0266119 | 5/1988 | |
| EP | 0302582 | 2/1989 | |
| EP | 0330180 | 8/1989 | |
| EP | 0333523 | 9/1989 | |
| EP | 0 334 062 A2 | 9/1989 | |
| EP | 0 374 531 A2 | 6/1990 | |
| EP | 0 451 390 | 10/1991 | |
| EP | 0451391 | 10/1991 | |
| EP | 0 467 389 A2 | 1/1992 | |
| EP | 0471036 | 2/1992 | |
| EP | 0 475 178 A1 | 3/1992 | |
| EP | 0531497 | 3/1993 | |
| EP | 0 635 261 A1 | 1/1995 | |
| EP | 0706792 | 4/1996 | |
| EP | 0737750 | 10/1996 | |
| EP | 0 779 072 A1 | 6/1997 | |
| GB | 2185979 A | 8/1987 | |
| GB | 2 234 896 A | 2/1991 | |
| GB | 2 265 311 A | 9/1993 | |
| GB | 2 310 801 A | 9/1997 | |
| WO | WO 90/11092 | 10/1990 | |
| WO | 91/11092 | 10/1990 | |
| WO | WO90/13361 | 11/1990 | ............ B01J/13/12 |
| WO | WO 91/19487 | 12/1991 | |
| WO | WO 92/06666 | 4/1992 | |
| WO | 93/19183 | 9/1993 | |
| WO | WO 94/04171 | 3/1994 | |
| WO | 94/04260 | 3/1994 | |
| WO | WO 94/09898 | 5/1994 | |
| WO | WO94/18954 | 9/1994 | ............ A61K/9/48 |
| WO | 94/23699 | 10/1994 | |
| WO | 94/23738 | 10/1994 | |
| WO | WO 94/23738 | 10/1994 | |
| WO | WO 94/28873 | 12/1994 | |
| WO | WO95/03356 | 2/1995 | ............ C08G/81/00 |
| WO | WO95/03357 | 2/1995 | .............. C08J/3/14 |
| WO | WO 95/05853 | 3/1995 | |
| WO | WO 95/07072 | 3/1995 | |
| WO | WO 95/11009 A1 | 4/1995 | |
| WO | WO 95/17167 | 6/1995 | |
| WO | 95/20660 | 8/1995 | |
| WO | 95/21250 | 8/1995 | |
| WO | WO95/21931 | 8/1995 | ............ C12N/15/87 |
| WO | 95/24929 | 9/1995 | |
| WO | 95/31184 | 11/1995 | |
| WO | 95/31187 | 11/1995 | |
| WO | 95/35097 | 12/1995 | |
| WO | 96/00295 | 1/1996 | |
| WO | WO 96/11671 | 4/1996 | |
| WO | WO 96/29998 | 10/1996 | |
| WO | WO 97/35563 A2 | 10/1997 | |
| WO | 97/36578 | 10/1997 | |
| WO | WO88/01213 | 2/1998 | ............ B23B/5/16 |

OTHER PUBLICATIONS

Walter et al., "Microencapsulation of DNA using poly(DL–lactide–co–glycolide): stability issues and release characteristics", Elsevier vol.61(1999) pp. 361–374.*

(List continued on next page.)

Primary Examiner—Dave T. Nguyen
(74) Attorney, Agent, or Firm—Fish & Richardson P.C.

(57) ABSTRACT

A microparticle contains DNA coding for a polypeptide and oral administration of the microparticle leads to its expression. DNA coding for an immunogen is for stimulating antibody formation in a recipient and DNA coding for a non-immunogenic polypeptide is for gene therapy applications. DNA is incorporated into the microparticle without destruction of its function.

28 Claims, 6 Drawing Sheets

U.S. PATENT DOCUMENTS

Figure 1:
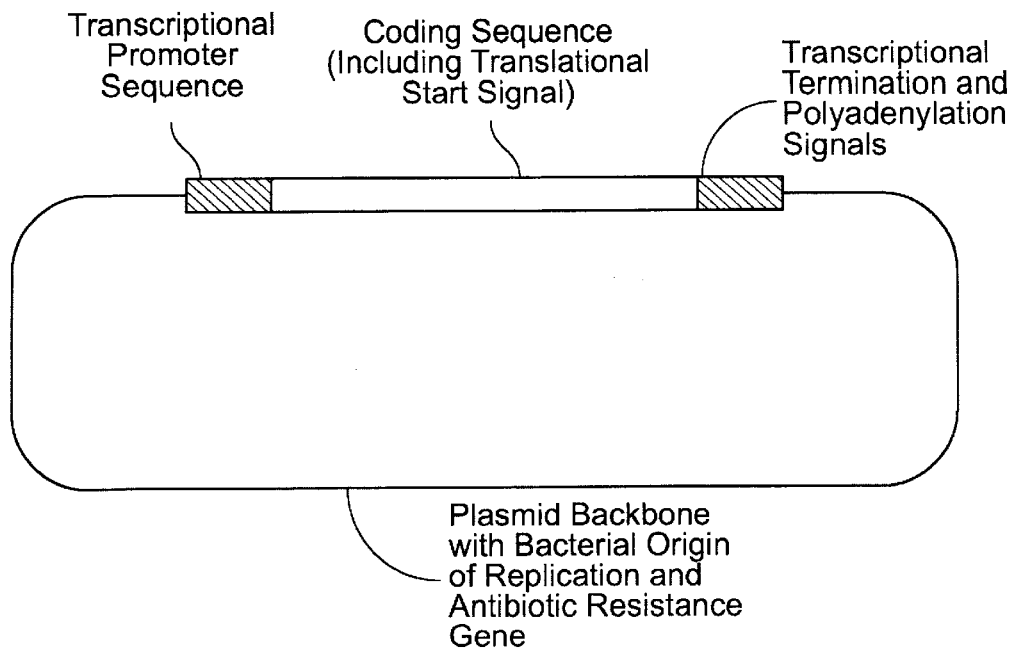

| | | | |
|---|---|---|---|
| 4,293,539 A | 10/1981 | Ludwig et al. | 424/19 |
| 4,623,588 A | 11/1986 | Nuwayser et al. | 428/402.24 |
| 4,652,441 A | 3/1987 | Okada et al. | 424/19 |
| 4,711,782 A | 12/1987 | Okada et al. | 424/455 |
| 4,741,872 A | 5/1988 | De Luca et al. | 264/4.7 |
| 4,818,542 A | 4/1989 | DeLuca et al. | 424/491 |
| 4,853,226 A | 8/1989 | Machida et al. | 424/426 |
| 4,897,268 A | 1/1990 | Tice et al. | 424/455 |
| 4,917,893 A | 4/1990 | Okada et al. | 424/423 |
| 4,933,105 A | 6/1990 | Fong | 252/303 |
| 5,061,492 A | 10/1991 | Okada et al. | 424/423 |
| 5,075,109 A | 12/1991 | Tice et al. | 424/88 |
| 5,084,553 A | 1/1992 | Hess et al. | 528/361 |
| 5,100,669 A | 3/1992 | Hyon et al. | 424/426 |
| 5,160,745 A | 11/1992 | De Luca et al. | 424/487 |
| 5,407,609 A | 4/1995 | Tice et al. | 264/46 |
| 5,417,986 A | 5/1995 | Reid et al. | 424/494 |
| 5,460,831 A | 10/1995 | Kossovsky et al. | 424/493 |
| 5,529,777 A * | 6/1996 | Andrianov et al. | 424/184.1 |
| 5,531,925 A * | 7/1996 | Landh et al. | 252/299.01 |
| 5,540,937 A | 7/1996 | Billot et al. | 424/489 |
| 5,580,859 A | 12/1996 | Felgner et al. | 514/44 |
| 5,585,050 A * | 12/1996 | Jorda et al. | 264/4.1 |
| 5,589,466 A | 12/1996 | Felgner et al. | 514/44 |
| 5,622,649 A * | 4/1997 | Hunter et al. | 252/309 |
| 5,639,473 A * | 6/1997 | Grinstaff et al. | 424/450 |
| 5,643,578 A * | 7/1997 | Robinson et al. | 424/210.1 |
| 5,643,605 A * | 7/1997 | Cleland et al. | 424/489 |
| 5,648,095 A * | 7/1997 | Illum et al. | 424/489 |
| 5,650,173 A | 7/1997 | Ramstack et al. | 424/489 |
| 5,654,008 A | 8/1997 | Herbert et al. | 424/489 |
| 5,656,469 A | 8/1997 | Tresco et al. | 435/182 |
| 5,665,383 A * | 9/1997 | Grinstaff et al. | 424/450 |
| 5,783,567 A | 7/1998 | Hedley et al. | 514/44 |
| 5,814,344 A | 9/1998 | Tice et al. | 424/501 |
| 5,820,883 A * | 10/1998 | Tice et al. | 424/501 |
| 5,853,763 A * | 12/1998 | Tice et al. | 424/489 |
| 5,942,252 A * | 8/1999 | Tice et al. | 424/501 |
| 6,024,983 A * | 2/2000 | Tice et al. | 424/501 |
| 6,080,429 A * | 6/2000 | Cleland et al. | 424/489 |
| 6,096,331 A | 8/2000 | Desai et al. | 424/422 |
| 6,159,502 A * | 12/2000 | Russell-Jones et al. | 424/489 |
| 6,217,908 B1 * | 4/2001 | Mathiowitz et al. | 424/493 |
| 6,248,720 B1 * | 6/2001 | Mathiowitz et al. | 514/44 |

OTHER PUBLICATIONS

Yung–Yueh Hsu et al., "Comparison of Process Parameters for Microencapsulation of Plasmid DNA in Poly(D,L–Lactic–co–Glycolic) Acid Microspheres", Journal of Drug Targeting vol. 7 No. 4 pp 313–323, 1999.*

Ledley (Human Gene Ther. (1995) 6:1129–1144).*

Gunzburg et al. (Molecular Medicine Today, pp. 410–417, 1995).*

Crystal (Science, vol. 270, :404–410, 1995).*

Robert Whalen (Emerging Infectious Diseases, vol. 2, No. 3:168–175, 1996).*

Etlinger, Immunology Today (1992), vol. 13, No. 2:52–55.*

Donald R. Cowsar et al., "Poly(lactide–co–glycolide) Microcapsules for Controlled Release of Steroids", Methods in Enzymology, 112,pp. 101–117 (May 1985).

Thomas M.S. Chang, "Biodegradable Semipermeable Microcapsules Containing Enzymes, Hormones, Vaccines, and Other Biologicals" Journal of Bioengineering, 1, pp. 25–32 (1976).

Jon A. Wolff et al. "Direct Gene Transfer into Mouse Muscle in Vivo" Science 247, 1465–1468 (1990).

R.A. Spooner et al. "DNA vaccination for cancer treatment", Gene Therapy 2, 173–180 (1995).

A.W. Wheeler et al. "Immunogenicity in Guinea Pigs and Tolerance in Grass Pollen–Sensitive Volunteers of Enteric–Coated Grass Pollen Allergens", Int. Archs. Allergy appl. Immun. 83, 354–358 (1987).

Takahiro Uchida et al. "Oral Delivery of Poly (lactide–co–glycolide) Microspheres Containing Ovlabumin as a Vaccine Formulation: Particle Size Study" Biol. Pharm. Bull. 17(9) pp. 1272–1276 (1994).

Alexakis, T. et al., "Microencapsulation of DNA With Alginate Microspheres and Crosslinked Chitosan Membranes for In Vivo Application," *Appl. Biochem. Biotech.* 50:93–106 (1995).

European Patent Office, English language abstract for Japanese Patent No. 06–009377.

Truong, V.L. et al., "Immuno–microsphere as Gene Delivery Vehicle: Targeting of LAMP–1 to Lysosomal Membrane," *Proceed. Intern. Symp. Control. Rel. Bioact. Mater.* 21:142–143 (1994).

Truong–Le, V.L. et al., "Gene Transfer by Gelatin–DNA Coacervate," *Proceed. Intern. Symp. Control. Rel. Bioact. Mater.* 22:466–467 (1995).

Amagi, M. et al., "Antibodies Against a Novel Epithelial Cadherin in Pemphigus Vulgaris, a Disease of Cell Adhesion," *Cell* 67:869–877 (1991).

Chen, S.C. et al., "Protective Immunity Induced by Oral Immunization with a Rotavirus DNA Vaccine Encapsulated in Microparticles," *J. Virol.* 72:5757–5761 (1998).

Eldridge, J.H. et al., "Biodegradable and biocompatible poly(DL–Lactide–co–glycolide) microspheres as an adjuvant for staphylococcal enterotoxin B toxoid which enhances the level of toxin–neutralizing antibodies," *Infect. Imm.* 59:2978–2986 (1991).

Eldridge, J.H. et al., "Controlled Vaccine Release in the Gut–Associated Lymphoid Tissues. 1. Orally Administered Biodegradable Microspheres Target the Peyer's Patches," *J. Controlled Release* 11:205–214 (1990).

Florence, A.T. "The Oral Absorption of Micro– and Nanoparticulates: Neither Exceptional Nor Unusual," *Pharm. Res.* 14:259–266 (Mar. 1997).

Gref, R. et al., "Biodegradable Long–Circulating Polymeric Nanopheres," *Science* 263:1600–1603 (1994).

Heard, "HLA and autoimmune disease," in *HLA and Disease*, Academic Press, San Diego, CA, chapter 7 (1994).

Hedly, M. L. "Genetic Modulation and Antigen Presentation," in *MHC Molecule: Expression, Assembly, and Function*, chapter 17 (1996).

Jacobs S.C. et al., "Protection elcited by a replication–defective adenovirus vector expressing the tick–borne encephalitis virus non–structural glycoprotein NS1," *J. Gen. Virol.* 75:2399–2402 (1994).

Jacobs, S.C. et al., "High–Level Expression of the Tick–Borne Encephalitis Virus NS1 Protein by Using an Adenovirus–Based Vector: Protection Elicited in a Murine Model," *J. VirOL.* 66:2086–2095 (1992).

Jepson, M. et al., "Comparison of Poly(DL–Lactide–co–Glycolide) and Polystyrene Microsphere Targeting to Intestinal M Cells," *J. Drug Targeting* 1:245–249 (1993).

Jeyanthi, R. et al., "Develpoment of a Biodegradable Microphere Formulation for the Sustained Release of a Bioactive Peptide," *Pharm. Res.* 8:151(S), pdd 7079 (1991).

Jones, D.H. et al., "Orally Administered Microencapsulated *Bordetella pertussis* Fimbriae Protect Mice from *B. pertussis* Respiratory Infection," *Infect. Immun.* 64:489–494 (Feb. 1996).

Jones et al., "Poly(DL–Lactide–co–glycolide)– encapsulated plasmid DNA elicits systemic and mucosal antibody responses to encoded protein after oral administration," *Vaccine 15*:814–817 (Jun. 1997).

Jones, et al., "Oral delivery of Poly(lactide–co–glycolide) encapsulated vaccines," *Behring Inst. Mitt.* 98:220–228 (Feb. 1997).

Jones, D.H. et al., "Immune Responses Following Oral and Parental Administration of Plasmid DNA Encapsulated in Poly(lactide–coglycolide) Microparticles," *Int. Meeting on Nucleic Acid Vaccines*, Bethesda, MD, Abstract and attached Figures 2 and 3 and Figure entitled Stool IgA Response to PLG–Encapsulated DNA (Feb. 5–7, 1996).

Jones, D.H. et al., "Orally Administered Microencapsulated *Bordetella Pertussis* Fimbriae Protect Mice from *B. Pertussis* Respiratory Infection," *Dev. Biol. Stand.* 92:149–155 (1998).

Jones, D.H. et al., "Protection of mcie from *Bordetella pertussis* respiratory infection using microencapsulated pertussis fimbriae," *Vaccine 13*:675–681 (May 1995).

Jones, D.H. et al., "PLG microencapsulation of vaccine antigens," *J. Biotech.* 44:29–36 (1994).

Kreuter, J. "Nanoparticles and microparticles for drug and vaccine delivery," *J. Anat.* 189:503–505 (Dec. 1996).

Lewis, K. et al., "Biodegradable poly(L–Lactic acid) matrices for the sustained delivery of antisense oligonucleotides," *J. Controlled Release 37*:173–183 (Nov. 1995).

Murphy, D. et al., "A novel MHC class II epitope expressed in thymic medulla but not cortex," *Nature 338*:765–768 (1989).

Neutra, M. et al., "Epithelial M Cells: Gateways for Mucosal Infection and Immunization," *Cell 86*:345–348 (Aug. 1996).

O'Hagan, D.T. "the intestinal uptake of particles and the implications for drug and antigen delivery," *J. Anat.* 189:477–482 (Dec. 1996).

Puyal, C. et al., "A new cationic liposome encapsulating genetic material. A potential delivery system for polynucleotides," *Eur J Biochem.* 228:697–703 (Mar. 1995).

Shimoda, S. et al., "HLA–DRB4 0101–restricted Immunodominant T Cell Autoepitope of Pyruvate Dehydrogenase Complex in Primary Biliary Cirrhosis: Evidence of Molecular Mimicry in Human Autoimmune Diseases," *J. Exp. Med.* 181:1835–1845 (May 1995).

Steinman, L. "Escape from 'Horror Autotoxicus': Pathogenesis and Treatment of Autoimmune Disease," *Cell 80*:7–10 (Jan. 1995).

Tomlinson, E. and Rolland, A.P. et al., "Controllable gene therapy Pharmaceutics of non–viral gene delivery systems," *J. Controlled Release 39*:357–372 (Mar. 1996).

Visscher, G.E. "Biodegradation of and tissue reaction to 50:50 Poly(DL–lactide–co–glycolide)microcapsules," *J. Biomed. Mater. Res.* 19:349–365 (1985).

Dialog File 351, Accession No. 81–32924D/198119, Derwent WPI English language abstract for Document AL1 (EP 0 027 662 A1), 1981.

Dialog File 351, Accession No.86–108252/198617, Derwent WPI English language abstract for Document AM1 (EP 0 179 023 A2), 1986.

Dialog File 351, Accession No.92–166845/199220, Derwent WPI English language abstract for Document AL3 (WO 92/06666), 1992.

Dialog File 351, Accession No.94–167187/199420, Derwent WPI English language abstract for Document AN3 (WO 94/09898), 1994.

Dialog File 351, Accession No.95–123218/199516, Derwent WPI English language abstract for Document AM4 (WO 95/07072), 1995.

Dialog File 351, Accession No.95–240449/199531, Derwent WPI English language abstract for Document AN4 (WO 95/17167), 1995.

Morris, W. et al., "Potential of polymer microencapsulation technology for vaccine innovation," *Vaccine*, vol. 12, No. 1, pp. 5–11 (1994).

Epstein, D.A. et al., "Alternative Delivery Systems For Peptides And Proteins As Drugs," *CRC Critical Review in Therapeutic Drug Carrier Systems*, vol. 5, Issue 2, pp. 99–139 (1988).

Rajasubramanian, Ganesh et al., "Fabrication of Resorbable Microporous Intravascular Stents for Gene Therapy Applications", *ASAIO Journal*, vol. 40, No. 3, pp. 584–589 (Jul. 1994).

Morris, William et al., "Potential of Polymer Micro–encapsulation Technology for Vaccine Innovation", *Vaccine*, vol. 12, No. 1, pp. 5–11 (Jan. 1994).

Sah, H. K. et al., "Biodegradable Microcapsules Prepared by a W/O/W Technique: Effects of Shear Force to Make a Primary W/O Emulsion on their Morphology and Protein Release", *Journal of Microencapsulation*, vol. 12, No. 1, pp. 59–69 (Jan. 1995).

Nellore, Ranjani et al., "Application of Biodegradable Microspheres to Hapatitis B Surface Antigen Vaccination System", *Pharmaceutical Research*, vol. 8, No. 10, p. S151, Abstract No. PDD 7098 (1991).

P. Marquet et al., "Toxicity of tungsten", *The Lancet*, vol. 349, pp 58–59 (Jan. 4, 1997).

D.L. Miller et al., "Comet Assay Reveals DNA Strand Breaks Induced by Ultrasonic Cavitation In Vitro", *Ultrasound in Med. & Biol.*, vol. 21, No. 6, pp. 841–848 (1995).

* cited by examiner

MICROENCAPSULATED DNA FOR VACCINATION AND GENE THERAPY

FIELD OF INVENTION

The present invention relates to microencapsulated DNA, to vaccines comprising microencapsulated DNA, to methods of vaccination and to methods of gene therapy comprising administration of DNA in microparticles, to methods of preparing microparticles containing DNA and to dried compositions comprising DNA-containing particles.

TECHNOLOGY REVIEW

The biodegradable polymer poly (DL-lactide-co-glycolide) (PLG) has been used for many years by the pharmaceutical industry to deliver drugs and biologicals in microparticulate form in vivo. The United States FDA has recently approved a PLG microsphere 30-day delivery system for leuprolide acetate (Lupran Depot (registered trade mark)) to be used in the treatment of prostate cancer. A useful review of the potential of polymer microencapsulation technology for vaccine use is found in Vaccine, 1994, volume 12, number 1, pages 5-11, by William Morris et al.

As an alternative to encapsulation, it is also known to deliver antigens in phospholipid vesicles called liposomes, as described for example by Eppstein, D. A et al in Crit. Rev. Ther. Drug Carrier Syst. 1988, 5(2), pages 99-139. It is reported that a number of antigens have been delivered intraperitoneally using liposomes, including cholera toxin, malaria sporozoite protein and tetanus toxoid, and that influenza antigen has been delivered intra-nasally.

It is also known that, in certain circumstances, injection of naked DNA into tissue can lead to expression of a gene product coded by that DNA. For example, in 1984, work at the United States NIH reported that intrahepatic injection of naked, cloned plasmid DNA for squirrel hepatitis produced both viral infection and the formation of anti-viral antibodies in the squirrels.

WO-A-95/05853 describes methods, compositions and devices for administration of naked polynucleotides which encode biologically active peptides. This published application describes, inter alia, the injection of naked DNA coding for an immunogenic antigen with the aim of raising antibodies in the recipient of the naked DNA.

Liposomal delivery of DNA is also known, and is described, for example, in EP-A-0475178.

An alternative method for obtaining expression of a desired gene product is described in EP-A-0161640, in which mouse cells expressing bovine growth hormone are encapsulated and implanted into a cow to increase milk production therein.

EP-A-0248531 describes encapsulating linear poly (I:C) in microcapsules and using these to induce production of interferon.

WO-A-94/23738 purports to describe a microparticle containing DNA in combination with a conjugate that facilitates and targets cellular uptake of the DNA. In working examples, bombardment of cells by microparticles containing Tungsten is described. These examples appear little different to conventional bombardment of cells with DNA-coated metal particles. Furthermore, sonication is proposed in microparticle manufacture, a step that is known to risk DNA damage but the presented data is inadequate and inappropriate to determine the integrity of the encapsulated DNA.

SUMMARY OF THE INVENTION

In the present invention, it is desired to deliver, in vivo, DNA encoding proteins with immunogenic, enzymatic or other useful biological activity, usually under the control of an active eukaryotic promoter. Objects of the invention include improvement on vaccination therapies known in the art and improvement upon prior art gene therapy methods.

Improvement of or alternatives to existing compositions and methods are desirable as these existing methods are known to contain a number of drawbacks.

WO-A-95/05853 describes administration of naked polynucleotides which code for desired gene products. However, the compositions and methods in this publication are suitable only for injection, requiring sterile procedures, being in itself an unpleasant and awkward route of administration.

WO-A-94/23738 purports to provide a process in which encapsulated DNA is released from the particles in the body of the recipient and then taken up by cells, although no accomplished in vivo examples are presented.

The invention seeks to provide novel compositions and methods of administration thereof that improve upon existing vaccination and gene therapy techniques and are effective in vivo, or at least overcome some of the problems or disadvantages identified in known compositions and methods.

It is known that DNA is readily damaged so that it is no longer capable of inducing expression of a gene product. Surprisingly, the inventors have succeeded in devising a technique for encapsulation of DNA within polymer particles, such that the DNA retains sufficient integrity to induce expression of a gene product coded thereby. The inventors have also succeeded in devising a DNA-containing microparticle suitable for mammalian vaccination or for gene therapy.

BRIEF DESCRIPTION OF THE DRAWINGS

FIG. 1 is a schematic diagram of the components of a protein-expressing plasmid suitable for incorporation into a DNA-containing capsule according to the invention;

FIG. 2 illustrates the results of Example 3, namely induction of luciferase-specific serum antibodies by PLG-encapsulated plasmid DNA, and in which the left column indicates antibody titre after 3 weeks with the right column showing antibody titre after 6 weeks (i.m. represents intra muscular, i.p. represents intra peritoneal, the bottom portion of each column represents IgG levels, the top portion resents IgM levels;

FIG. 3 shows dose-response data for injected and oral doses of encapsulated DNA, with the titre of IgG, IgM and IgA in each case;

FIG. 4 shows: A—agarose gel dectrophoresis of plasmid DNA following homogenisation in a Silverson mixer at 2000 and 8000 rpm for 0-300 seconds; and B—agarose gel dectrophoresis of DNA before and after encapsulation; and FIG. 5 shows stool IgA response to DNA within PLG microparticals.

FIG. 6 shows the results of oral administration of PLG-encapsulated DNA expressing measles virus N protein; and FIG. 7 shows the results of oral administration of PLG-encapsulated DNA expressing rotavirus VP6 gene: A—faecal rotavirus—specific IgA response, B—rotavirus shedding after challenge of orally immunized mice.

DETAILED DESCRIPTION OF THE INVENTION

Accordingly, a first aspect of the invention provides a pharmaceutical composition comprising DNA encapsulated in a polymer, said DNA comprising a sequence coding for a polypeptide and wherein the composition is adapted to induce expression in a recipient of the coding sequence. Preferably, the coding sequence is accompanied by a promoter promoting expression of the sequence. Where the pharmaceutical composition is for use on mammals, it is convenient to use a eukaryotic promoter and especially a promoter that operates in a wide variety of tissue types. In particular embodiments of the invention, a tissue—or cell type—specific promoter is used.

In use, the pharmaceutical composition is orally administered, and the coding sequence is expressed leading to desired therapeutic effects.

A composition of the invention suitable for vaccination contains a sequence coding for an immunogen. Following administration of the composition, expressed immunogen elicits production of antibodies within the recipient, thereby contributing to vaccination of the recipient.

A specific embodiment of the invention, described in an example below, contains a DNA sequence coding for a protein. It has been administered in vivo and has been found to induce expression in a mammal of that protein. The expression was detected by measurement of production of antibodies specific for that protein. The composition of the specific embodiment comprises microparticles in the size range up to about 10 $\mu$m.

Generally, the microparticles of the invention are intended to enter cells of the recipient by phagocytosis, for example phagocytosis by macrophages or other antigen presenting cells. Subsequently, the body of the microparticle breaks down in the intracellular space and the DNA is released. It is preferred that the microparticles of the invention are in the size range 0.01 $\mu$m to 30 $\mu$m, with 1 $\mu$m to 10 $\mu$m being a more preferred range. These sizes have been found to be suitable for reliably achieving in vivo expression of the DNA. It is also to be noted that agents promoting uptake of the DNA are not needed in microparticles of the invention—as the microparticle size determines its uptake.

An alternative composition, according to the invention, contains a sequence coding for a non-immunogenic product. Such a composition is particularly useful for gene therapy, wherein it is desired to express in a recipient a gene product that is non-expressed, or expressed at a level that it is desired to increase. In this case, a composition of the invention comprises a DNA sequence coding for a desired product, and wherein following administration of the composition expression of the coding sequence results in an increased level of the desired product, giving the gene therapy effect.

It is again a feature of the invention that microparticles for gene therapy applications have sizes in the range 0.01 $\mu$m to 30 $\mu$m, preferably 1 $\mu$m to 10 $\mu$m, to target their uptake by phagocytosis.

Specific embodiments of the invention, for use in vaccination, comprise a DNA sequence coding for a protein or an immunogenic component thereof, or an immunogenic fragment or variant thereof, of a virus, bacterium or other pathogenic microorganism. The protein is, for example, an HIV protein, an influenza virus protein, a measles virus protein, a hepatitis virus protein (such as hepatitis surface antigen) or a pertussis protein. Further, where the composition is for oral use, it can conveniently also contain a taste-enhancing agent. The term "taste-enhancing agent" is intended to encompass sweeteners, flavourings and agents that mask any unpleasant taste from other components of the composition. It can conveniently be enterically coated or co-administered with an appropriate antacid formulation.

In a specific embodiment described below, a preparation of microparticles contains a DNA sequence coding for a measles protein. Oral administration of the microparticles elicited an increase in antibodies specific for that protein. Likewise, another microparticle preparation contains a DNA sequence coding for a rotavirus protein. Oral administration of these microparticles preparation elicited anti-rotavirus protein antibodies and a protective effect against challenge by the virus.

Specific embodiments of the invention, suitable for gene therapy, comprise a DNA sequence coding for an enzyme or another protein needed for the treatment of genetic disease. For example, a DNA sequence coding for glucocerebrosidase is suitable for the treatment of Gaucher's disease.

The inventors have thus provided DNA encapsulated within a polymer such that the ability of DNA to code for a desired gene product is substantially not affected by the encapsulation process. It is known that DNA can readily be damaged by emulsifying and other steps necessary for production of polymer particles. The inventors have provided for encapsulation of DNA such that sufficient operative DNA is encapsulated for a biological effect to be obtainable upon administration of the encapsulated DNA.

The invention offers advantages, in that encapsulated DNA is suitable for oral administration, avoiding the unpleasant and awkward aspects associated with having to inject DNA preparations described in the prior art. Specific embodiments in examples described below have been successful in inducing immunogen-specific antibodies in response to oral administration of a composition of the invention. In addition, the encapsulated DNA formulation is suitable for drying, e.g. freeze drying, into a form that is stable over long periods and is suitable for storage. Further, for many vaccine applications it would be advantageous if, as well as a systemic humoral and cell—mediated immune response, immunity at mucosal surfaces could also be evoked. Specific embodiments of the invention, described below, have been demonstrated to elicit significant increases in specific IgA antibodies, following oral administration. The invention thus provides a pharmaceutical composition comprising DNA within a polymer particle, the DNA encoding a polypeptide, and the composition being adapted to induce mucosal polypeptide specific IgA antibodies in a recipient.

The polymer of the microparticle of the invention preferably is both biodegradable and non-toxic. Suitable polymers include lactide containing polymers and glycolide containing polymers and copolymers of 0-100:100-0 lactide:glycolide. In a specific embodiment of the invention, the polymer comprises poly (DL-lactide-co-glycolide), otherwise referred to as PLG, chosen as it has been approved for human and veterinary use.

The products of the invention are typically for in vivo use on animals, in particular animals. The polymer of the microparticle should therefore be non toxic in vivo and suitable for pharmaceutical use. The polymer should further be biodegradable—either by consisting of or comprising biodegradable polymer—so that it releases its DNA in the recipient. There exists in the art an extensive literature on polymers suitable for human and animal oral use and a person of skill in the art will be able to adapt polymers of the art into the microparticles of the present invention without difficulty. In this connection, the disclosures of EP-A-0451390, WO-A-95/31184 and WO-A-95/31187 are incorporated herein by reference.

The DNA contained within the particle will typically comprise double stranded DNA. The construction of a suitable DNA sequence for use in the invention will be appreciated by persons of skill in the art. It is preferred that the sequence comprises both a transcriptional promoter and a gene coding sequence. It is further preferred that the DNA sequence provides for a transcription termination and polyadenylation downstream of the coding sequence.

It is particularly preferred that the DNA be double stranded, circular and super coiled. It has been observed that during manufacture of particles the DNA is subjected to severe shear forces. Using particular mild particle manufacturing conditions, the inventors have managed to retain functional DNA, though have observed that previously supercoiled DNA may become partly converted to the open circular form in the process.

Plasmid DNA is particularly suitable and is used in the specific embodiments of the invention described below. As there is extensive literature relating to plasmid manufacture a person of skill in the art will readily be able to prepared a plasmid suitable for the microparticle of the invention. In general, plasmids incorporating any eukaryotic promoter sequence are suitable.

A further optional feature of the invention is that DNA—containing polymer particles can be manufactured so as to have different half-lives in vivo. When administering an antigen during vaccination, it may be advantageous for the antigen to be delivered over as long a time frame as possible. A particular embodiment of the invention provides a vaccine comprising first and second vaccine components, the first vaccine component comprising polymer-encapsulated DNA wherein the DNA includes a sequence coding for an immunogen and wherein the polymer has a first half life in vivo, and a second vaccine component comprising polymer—encapsulated DNA, wherein the DNA contains a sequence coding for an immunogen and wherein the polymer has a second half-life in vivo. The respective half-lives could be up to 5 days and more than 5 days. In one example, the immunogen of the first and second vaccine components are the same. Alternatively, the respective vaccine components can contain DNA sequences coding for different immunogens.

In an embodiment of the invention, the half-lives of the respective first and second vaccine components are up to two days, and more than two weeks. In a further embodiment, the first and second half-lives differ by at least an order of magnitude.

In use of a specific embodiment of the invention, described in an example below, a plasmid encoding luciferase is under control of the human cytomegalovirus immediate early promoter and is encapsulated within PLG in particles around two $\mu$m in size. This encapsulated DNA was administered to mice and elicited anti-luciferase antibodies that were detected over a period of several weeks. The production of antibodies in response to encapsulated DNA according to the invention was compared with antibody production in response to administration of naked DNA intraperitoneally and orally. In both cases, encapsulated DNA elicited equivalent or significantly higher amounts of IgG and IgM, and also evoked a significant IgA response.

A second aspect of the invention provides a method of encapsulating DNA in a polymer such that biological activity of the DNA is retained to a significant extent. In an embodiment of the second aspect, a method for encapsulating DNA within a polymer particle, said DNA being capable of inducing expression of a coding sequence within said DNA, comprises preparing a (water-in-oil)-in-water emulsion to form microparticles and separating subsequently produced DNA-containing microparticles by centrifugation. Resultant microparticles preferably have sizes in the range 0.01 $\mu$m to 30 $\mu$m, more preferably 1 $\mu$m to 10 $\mu$m.

The method of the invention is carried out under conditions that ensure at least a portion of the DNA is not damaged during manufacture of the particles and thereby retains its ability to induce expression of its gene coding sequence.

It is essential that DNA is incorporated into the microparticles, and DNA incorporation is increased by preparing a solution of DNA plus an alcohol, adding microparticle polymer and forming microparticles therefrom. The alcohol content of the solution suitably varies between 1% and 60% and preferably between 5% and 40%. In specific embodiments of the invention the alcohol content is around 15-35%, more particularly 20-30% for microparticles made from PLG, producing DNA incorporation of 25% and above, up to 50-60%. Ethanol is particularly suitable; methanol and propanol and other alcohols that do not denature DNA are also suitable, and the alcohol is preferably a straight chain or branched $C_2$-$C_{10}$ alcohol.

It is also preferred that the emulsification step or steps of the method be carried out under conditions of reduced shear stress, and this is optionally achieved by use of an emulsifying speed that is sufficient to obtain an emulsion and to form microparticles in the desired size range but not so high that all DNA is damaged by excessive shear. In an embodiment of the invention described below the emulsifying mixer speed is modified so that at least 25% DNA activity (assayed by transformation of competent bacteria or transfection of cultured cells) is retained in the resultant microparticles that contain DNA. Suitable speeds are below 8000 rpm, preferably below 6000 rpm, and in a specific embodiment described below the speed is about 3000 rpm.

The method may be performed at ambient temperature, which is convenient for laboratory and industrial purposes, and may also be performed at below ambient temperature improves the stability of the plasmid DNA during the encapsulation procedures. The temperature of the method may be reduced to below 20° C., below 10° C. or even below 5° C. In an embodiment of the invention, the method is carried out at below ambient temperature using a reduced amount of microparticle precursor compared to the amount used at ambient temperature.

The parameters of the method are thus chosen to promote formation of microparticles of 10 $\mu$m diameter or less and to promote incorporation of DNA into microparticles, and to avoid damage to the DNA such that the DNA can not be expressed in the recipient.

For any particular choice of polymer and DNA variations in the method may be necessary to obtain best results. The efficiency of a method can be assessed by transformation or transfection assays. In the transformation assay used by the inventors, DNA is recovered from microparticles by dissolution with organic solvent, quantitated and used to transform bacteria—ampicillin selection determines successful transformants. In the transfection assay, recovered DNA is used to transfect eukaryotic cells in culture, which culture is then assayed for presence of the antigen or gene therapy product. These assays have demonstrated that DNA recovered from microparticles produced by the method of the invention can retain 50-60% and up to 80% of the activity of the original DNA, indicating high efficiency of incorporation of functional DNA into microparticles.

In a further embodiment of the invention there is provided a method of making a pharmaceutical composition comprising preparing a DNA construct for expression of a coding sequence within the construct, and forming around the construct a polymer particle of size between 0.01 μm and 30 μm, wherein the construct remains capable of inducing expression of the coding sequence. In use, when the construct is separated from the particle, it induces expression of the coding sequence. The particle is preferably formed by emulsifying a solution of a polymer plus DNA plus alcohol.

The method of the invention is adapted to produce pharmaceutical compositions of the first aspect of the invention. The steps of the method are adapted so that, in a resultant composition which contains many DNA containing polymer particles, a useful proportion of particles contain active DNA, i.e. DNA that has not been damaged by the method such that its ability to induce expression of its coding sequence is lost. DNA activity is measured as a percentage of activity prior to the particle forming step.

An acceptable level of DNA biological activity is at least 10% and preferably at least 25%, though for particularly fragile DNA a lower percentage may be acceptable so long as, in use, a therapeutic effect is demonstrated by the composition.

In a specific embodiment of the invention, a composition is made by preparing a solution of a plasmid of double stranded, supercoiled DNA comprising a coding sequence and a eukaryotic promoter. Separately, a polymer solution is prepared. The two solutions are mixed together and emulsified at a speed between 1000 and 4000 rpm. A solution of a stabilizing agent is then added and the new mixture emulsified at a speed between 1000 and 4000 rpm. After centrifugation and resuspension of particles the DNA within retains 25% of its activity.

A third aspect of the invention provides a pharmaceutical composition comprising polymer—encapsulated DNA and having a reduced water content, such as less than 5% by weight. This composition is suitable for long term storage while retaining the ability of the DNA, upon administration to a recipient, to induce expression of a coding sequence within said DNA.

A method of preparing a pharmaceutical composition for storage, is to dry, such as by freeze drying, a pharmaceutical composition according to the first aspect of the invention. It is preferred that the dried composition has a water content of less than 5%, though the precise water content will be determined by the period of drying used.

A fourth aspect of the invention provides a method of vaccination comprising administering a vaccine according to the first aspect of the invention. Vaccination can thus be obtained by eliciting antibodies to the immunogen expressed from the gene coding sequence. As will be appreciated, the immunogen can be a component of a virus or bacterium or other pathogenic microorganism, or can be

EXAMPLES an analogue of said immunogen such that antibodies against the analogue are effective against the pathogen itself.

In a specific embodiment of the invention described in an example below, the particle material is PLG. The size of particles produced by the method of the invention are generally in the range of 0.01-30 μm, preferably 1-10 μm. Other suitable polymer formulations for DNA—containing particles according to the present invention include poly-lactic acid, poly-hydroxybutyrate, poly hydroxyvalerate, poly (hydroxybutrate/valerate), ethyl cellulose, dextran, polysaccharides, polyalkylcyanoacrylate, poly-methyl-methacrylate, poly(e-caprolactone) and mixtures of all of these components.

In use of a specific embodiment of the invention, described in an example below, a preparation of microparticles according to the invention comprises DNA coding for the protein luciferase. As will be appreciated by a person of skill in the art, a wide range of DNA sequences and constructs are suitable for use in this invention. In particular, the invention can be practised incorporating a wide range of plasmid vectors already well known and characterised in the art. Typically, a plasmid vector used in this invention will include a cDNA that codes for the desired gene product. The selection of additional components for the DNA sequence, such as promoters, reporter genes and transcription termination sequences can be made by a person of skill in the art according to common general knowledge concerning construction of known plasmid vectors.

The preferred administration route for compositions of the invention is the oral route, meaning that compositions of the invention should preferably be designed to avoid significant degradation while passing through the stomach with its high acid levels. It is known that uptake of microparticles of less than 10 μm in size occurs, inter alia, in the M cells of the intestine, and thus inclusion of DNA containing particles in this size range can be advantageous in promoting uptake at this intestinal location. Other modifications to the nature and character and components of the polymer can be made within the concept of the invention.

There now follows description of specific embodiments of the invention, accompanied by figures in which:

FIG. 1 is a schematic diagram of the components of a protein-expressing plasmid suitable for incorporation into a DNA-containing particle according to the invention;

FIG. 2 illustrates the results of example 3, namely induction of luciferase-specific serum antibodies by PLG-encapsulated plasmid DNA, and in which the left column indicates antibody titre after 3 weeks and the right column indicates antibody titre after 6 weeks (i.m. represents intra muscular, i.p. represents intra peritoneal, the bottom portion of each column represents IgG levels, the top portion represents IgM levels);

FIG. 3 shows dose-response data for injected and oral doses of encapsulated DNA, with the titre of IgG, IgM and IgA in each case.

FIG. 4 shows: A—agarose gel electrophoresis of plasmid DNA following homogenisation in a Silverson mixer at 2000 and 8000 rpm for 0-300 seconds; and B—agarose gel electrophoresis of DNA before and after encapsulation;

FIG. 5 shows stool anti-luciferase IgA response to DNA within PLG microparticles.

FIG. 6 shows the results of oral administration of PLG-encapsulated DNA expressing measles virus N protein; and FIG. 7 shows the results of oral administration of PLG-encapsulated DNA expressing rotavirus VP6 gene: A—faecal rotavirus—specific IgA response, B—rotavirus shedding after challenge of orally immunized mice.

Example 1

Method for Encapsulation of Plasmid DNA in PLG Microparticles Equipment:

1) Silverson Laboratory mixer with ¾" probe fitted with emulsor screen.
2) High speed centrifuge.
3) Normal laboratory glassware, beakers, measuring cylinders, stirrers etc.

Reagents:

1) Poly(lactide-co-glycolide) (PLG) solution—500 mgs in 3 ml dichloromethane.

2) Plasmid DNA (12 mg/ml in water).
3) Polyvinyl alcohol (PVA) solution (8% w/v in water).
4) Absolute ethanol.
5) TEN buffer (10 mM tris pH 8.0+1 mM EDTA+50 mM NaCl).

Method:
1) Mix 200 µl plasmid DNA solution with 250 µl of TEN and add 150 µl ethanol with stirring. Mix well.
2) Add this mixture to 3 ml PLG solution and emulsify in the Silverson mixer at 3000 rpm for 2 min.
3) Add this emulsion to 100 ml PVA and emulsify at 3000 rpm for 2 min.
4) Add the double emulsion to 1 litre of water and stir vigorously for 1 min.
5) Distribute the suspension of microparticles in centrifuge containers and centrifuge at $10,000 \times g_{av}$ for 30 mins.
6) Resuspend the microparticle pellet in 25 ml of water and homogenise with a hand homogeniser with large clearance (0.5 mm) to make a homogeneous suspension. Dilute with 200 ml of water and recentrifuge as above.
7) Repeat step 6 three times.
8) Resuspend the microparticle pellet in 25 ml of water as above, transfer to a vessel suitable for freeze drying, shell freeze in an isopropanol/dry ice mixture and lyophilise for 48 h.

In this method, steps 1-3 are carried out at ambient temperature. DNA was incorporated into the microparticles with an efficiency of about 25%.

Example 2

Plasmids for the Expression of Proteins after in vivo Delivery

Suitable plasmids for use in microparticles according to the invention consist of the following components (see FIG. 1):

1. Plasmid Backbone The plasmid backbone has an origin of replication and an antibiotic resistance gene or other selectable marker to allow maintenance of the plasmid in its bacterial host. Backbones providing a high copy number will facilitate production of plasmid DNA. An example would be from the pUC plasmid vectors.

2. Transcriptional Promoter Sequence Expression of the desired protein will be driven by a, typically eukaryotic, transcriptional promoter initiating the synthesis of mRNA. Generally, strong promoters functioning in a wide variety of tissue types and animal species are to be used, e.g. the human cytomegalovirus immediate early (hCMV IE) promoter. However, particularly for gene therapy applications, a tissue—or cell type—specific promoter may be more appropriate.

3. Coding Sequence The coding sequence contains the DNA sequence encoding the protein of interest. It contains the translational start codon ATG in sequence context favourable for initiation of protein synthesis. The coding sequence ends with a translational termination codon. Proteins to be expressed include a) reporter enzymes (e.g. luciferase, β-galactosidase); b) components of pathogenic microorganisms capable of inducing protective immune responses (e.g. the NS1 protein of tick-borne encephalitis virus, the N, H or F proteins of measles virus, the gp 120 protein of human immunodeficiency virus 1); c) enzymes or other proteins intended for the treatment of genetic disease (e.g. glucocerebrosidase for the treatment of Gaucher's disease).

4. Transcription Termination Sequence Improved expression levels are obtained under some circumstances when sequences causing termination of mRNA transcription are incorporated downstream of the coding sequence. These sequences frequently also contain signals causing the addition of a poly A tail to the mRNA transcript. Sequences which can be used in this role can be derived from the hCMV major immediate early protein gene or from SV40 viral DNA or elsewhere.

Example 3

We have constructed a plasmid encoding the insect protein luciferase, under the transcriptional control of the human cytomegalovirus immediate early (hCMV IE) promoter, and demonstrated luciferase activity in cells transfected in vitro.

We encapsulated purified plasmid DNA in PLG microparticles around 2 µm in size with moderate (about 25%) efficiency using the protocol of Example 1. Agarose gel electrophoresis indicates that a proportion of the initially closed circular supercoiled DNA undergoes conversion to a more slowly migrating form, probably relaxed circles, as a result of shear stresses in the encapsulation process. The encapsulated DNA was released from the particles and shown to retain a significant fraction of its in vivo biological activity in assays of bacterial transformation by electroporation, and luciferase expression after transfection into cultured cells.

Microencapsulated DNA (50 µg) was administered to mice by intraperitoneal (i.p.) injection and orally. Control animals received unencapsulated DNA by the same routes, and as a positive control by standard intramuscular (i.m.) injection. Luciferase-specific serum antibodies were analyzed by ELISA three and six weeks after DNA administration. Results are presented in FIG. 2.

Figure 2:
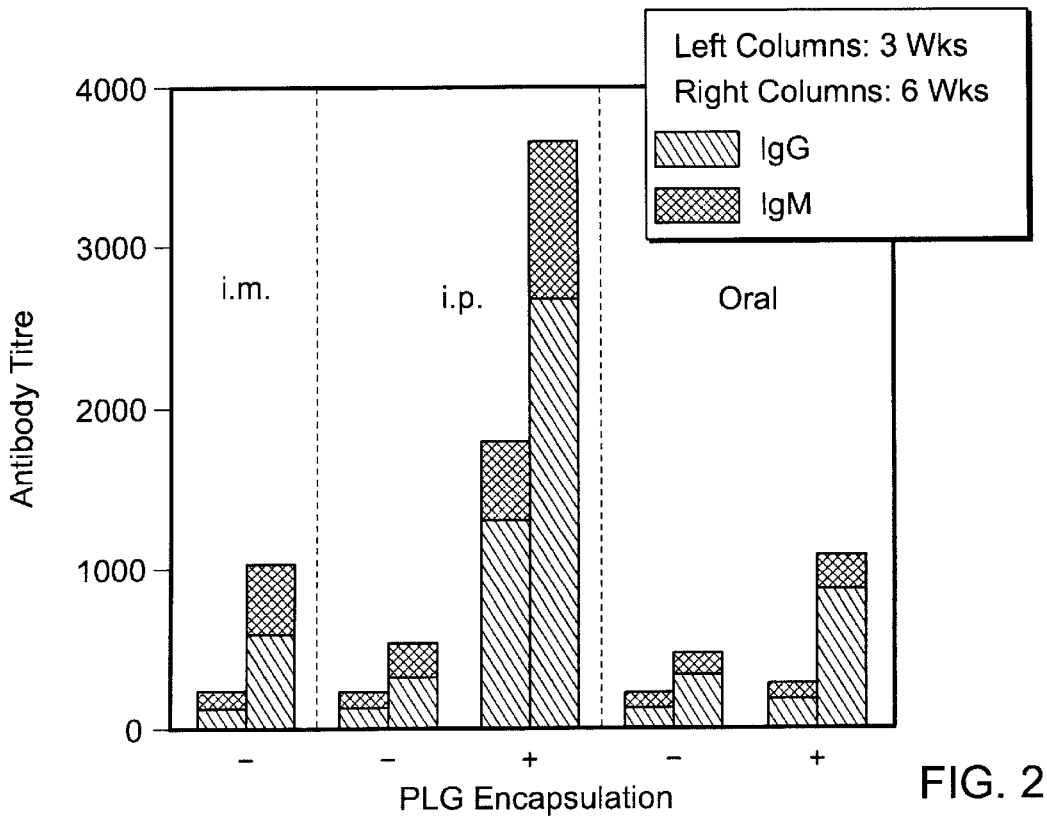

As shown in FIG. 2, modest specific IgG and IgM responses were seen after i.m. injection, as might be expected. Encapsulated DNA evoked strong IgG and IgM responses after i.p. injection, while unencapsulated DNA gave much weaker responses. Similarly, orally administered encapsulated DNA evoked a good IgG response which was not matched by unencapsulated DNA. The IgG and IgM antibody responses indicate that luciferase expression and presentation to the immune system occur after administration of plasmid DNA encapsulated in PLG microparticles with efficiencies exceeding that seen with the standard i.m. route, and exceeding that seen in comparative administration of unencapsulated DNA.

Example 4

In further experiments, microencapsulated DNA, made by the method of Example 1, in a range of doses (1-50 µg DNA) was administered to groups of outbred mice by intraperitoneal (i.p.) injection or orally. Luciferase-specific serum antibodies of IgG, IgM and IgA classes were analysed by ELISA at 3, 6 and 9 weeks after DNA administration.

Figure 3:
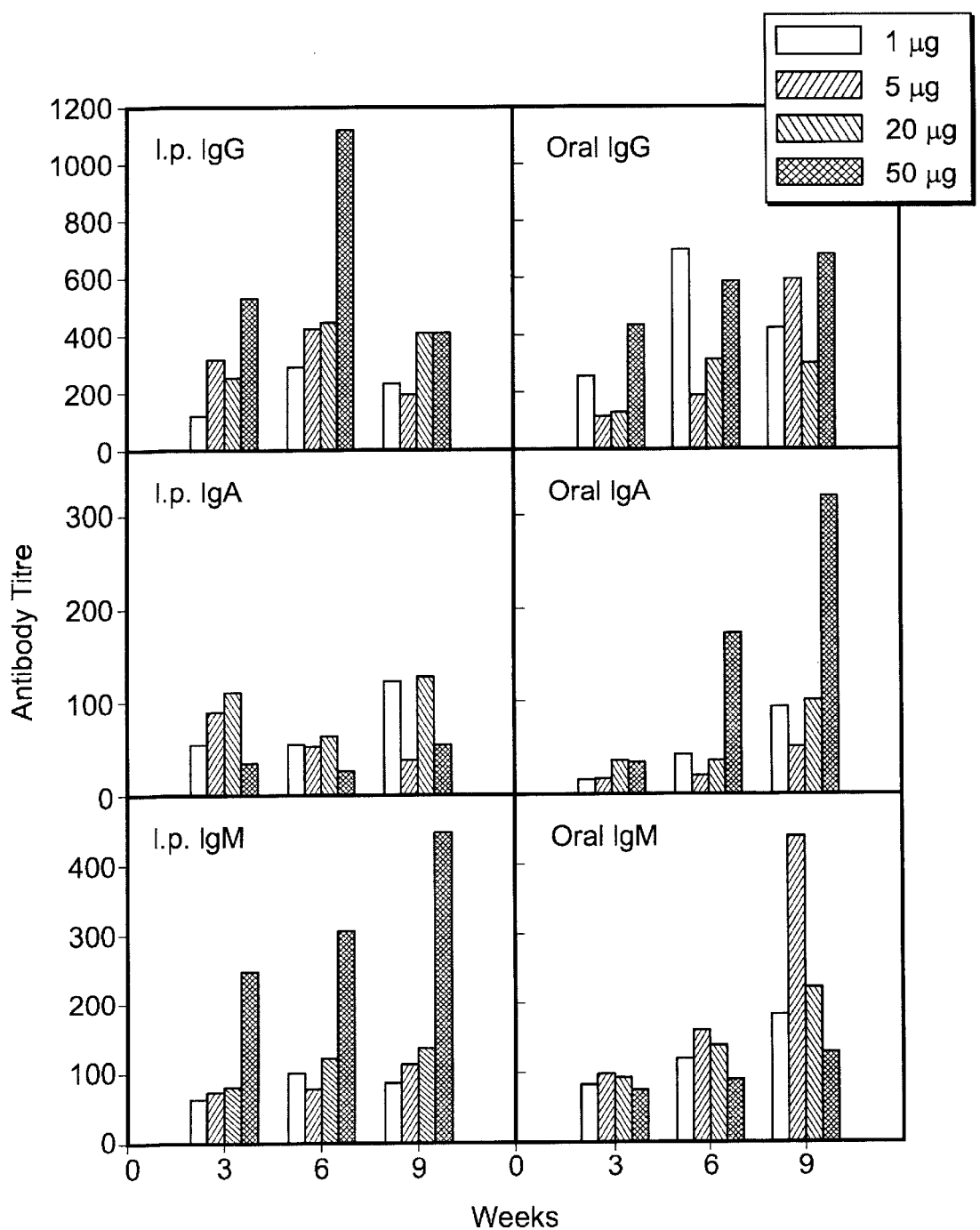

In FIG. 3, it can be seen that i.p. injection of PLG-encapsulated DNA evoked good IgG and IgM responses, and a modest IgA response. Orally administered encapsulated DNA evoked good responses in all three antibody classes. There is a trend for the antibody titres to increase with time after DNA administration, and the responses are also dose-related to a greater or lesser extent. It is apparent that quantities of DNA as low as 1 µg are able to evoke significant responses, especially at longer times after administration. These antibody responses again confirm that luciferase expression occurs after administration of plasmid DNA encapsulated in PLG microparticles, either by i.p. injection or orally. They also demonstrate that antigen is presented to the immune system by these means in such a fashion as to evoke IgG, IgM and IgA classes of antibody.

Example 5

We examined the effect of high-speed homogenisation steps, used to generate the required water-oil-water emulsions which are intermediates in the encapsulation process, on the physical integrity and biological function of plasmid DNA.

Figure 4B:
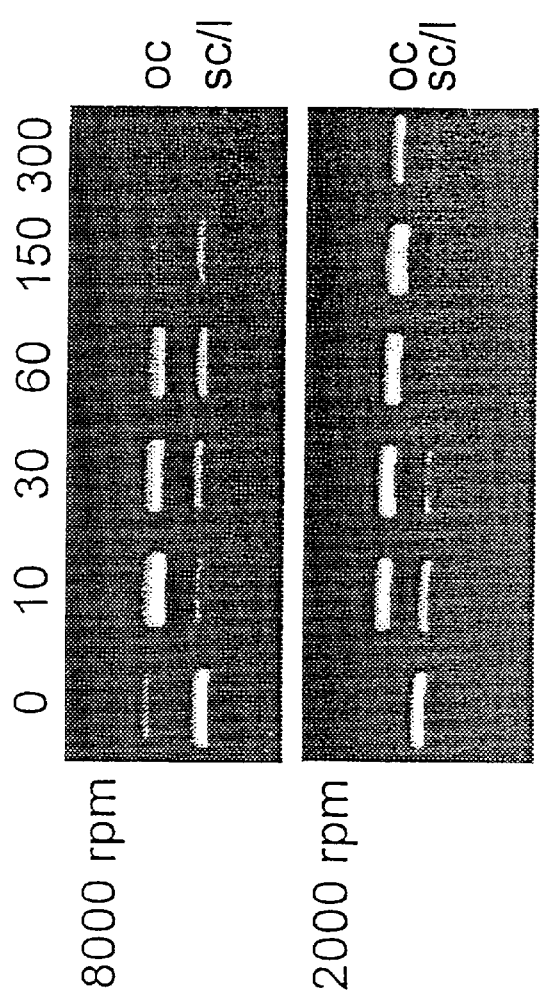
Figure 4A:
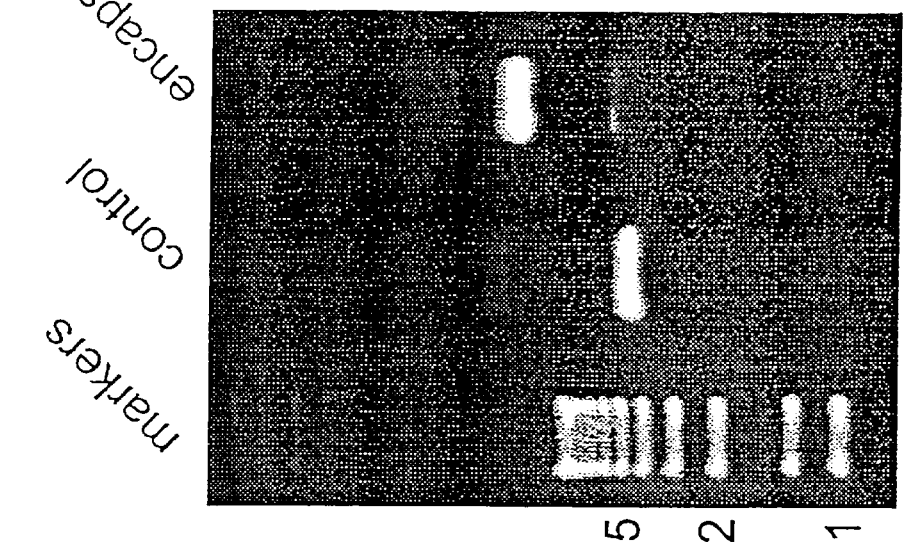

In initial experiments, supercoiled plasmid DNA was adjusted to concentrations and volumes similar to those to be used in microencapsulation experiments, and homogenised with a Silverson laboratory homogeniser. Samples were removed at intervals from 0 to 300 sec for analysis by agarose gel electrophoresis (FIG. 4A). Such an analytical procedure is capable of distinguishing between supercoiled (sc) DNA, open circular (oc) DNA, where a single strand has been nicked, and linear (I) DNA, where both strands have been cut at adjacent points (see, for example, FIG. 2C in Garner and Chrambach 1992. Resolution of circular, nicked and linear DNA, 4.4 kb in length, by electrophoresis in polyacrylamide solutions. *Electrophoresis* 13, 176-178). It is clear that exposure to such conditions for periods as short as 10 sec results in conversion from sc to oc form. At 8000 rpm, further conversion to the linear form and eventually more extensive degradation occur. However, at the reduced speed of 2000 rpm the oc form of DNA is relatively stable over the time period typically required for formation of the emulsion intermediates involved in PLG encapsulation. These studies thus show that plasmid DNA is vulnerable to shear-induced damage, and careful attention is required to the precise conditions to obtain encapsulation of minimally altered DNA.

From this basis, we have developed conditions for the encapsulation of purified plasmid DNA in PLG microparticles around 2 $\mu$m in size with moderate (about 25%) efficiency. Agarose gel electrophoresis (FIG. 4B) indicates that the initially closed circular supercoiled DNA undergoes conversion to the oc form, as a result of shear stresses in the encapsulation process. Biological activity of DNA released from microparticles has been assessed in assays of bacterial transformation by electroporation, and luciferase expression after transfection into cultured cells. DNA released from the particles retains a significant fraction (about 25%) of its in vitro activity in both these assays.

Example 6

Figure 5:
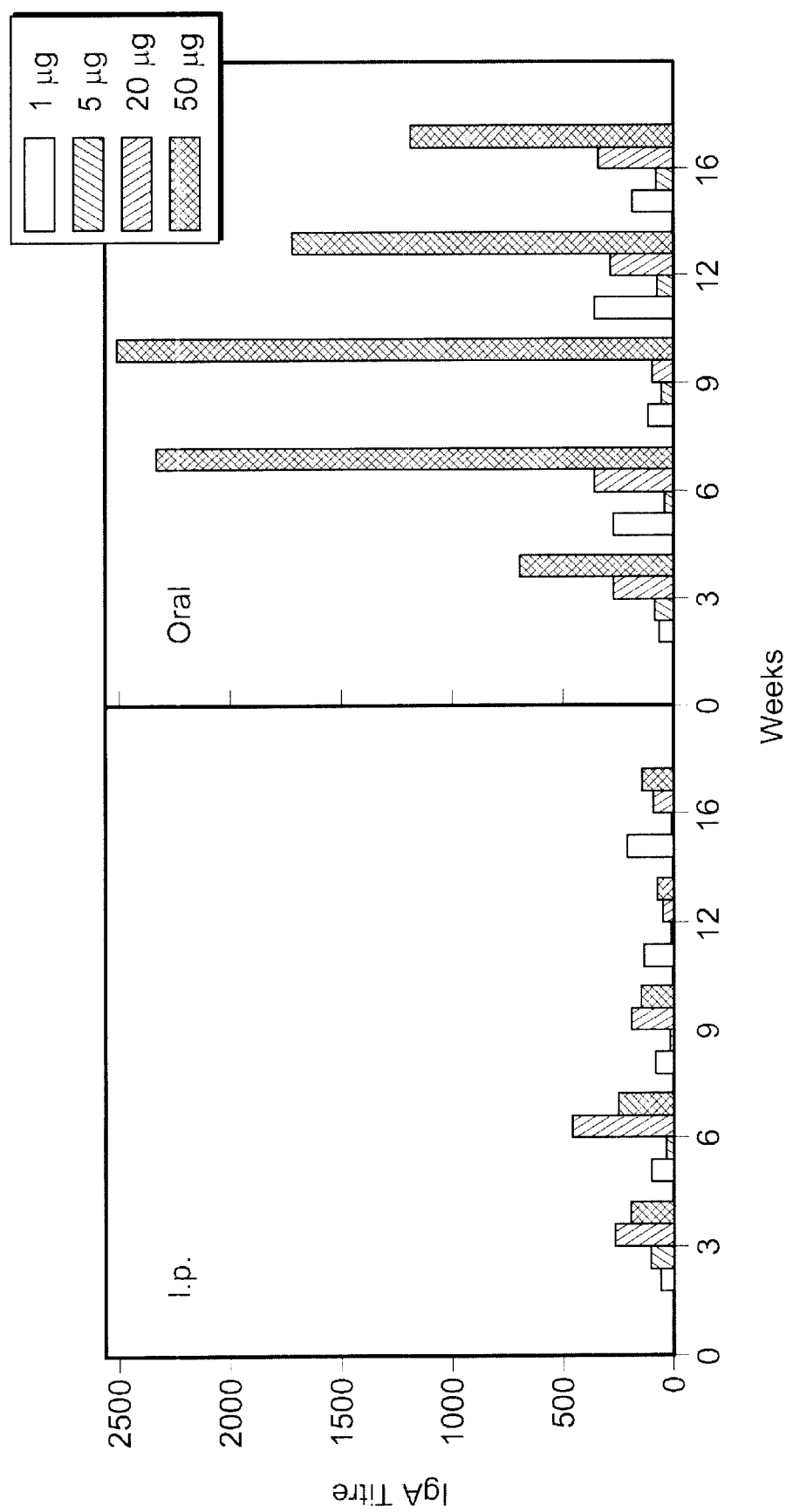

PLG-encapsulated DNA coding for luciferase, made by the method of Example 3, is also able to evoke a mucosal immune response to the expressed protein. Levels of IgG, IgM and IgA antibodies specific for luciferase were assessed by ELISA in stool samples from mice which received i.p. or oral doses of 1, 5, 20 or 50 $\mu$g of PLG-encapsulated DNA. No significant levels of IgG or IgM antibodies were found in stool samples from any group of mice. Rather limited IgA responses were seen in the i.p.-injected mice; however, oral administration resulted in significant levels of luciferase-specific IgA antibodies in the stool samples (FIG. 5). These reached extraordinarily high levels in those mice which received 50 $\mu$g PLG-encapsulated DNA. These results indicate that oral administration of a single dose of PLG-encapsulated plasmid DNA is capable of evoking a mucosal, as well as a systemic antibody response. This may be a useful attribute of a PLG-encapsulated DNA vaccine in applications where protection against infection at mucosal surfaces is desirable, as for measles or AIDS.

Example 7

We have exploited a plasmid expressing the measles virus (MV) nucleocapsid protein (N) to extend our observations that the oral administration of encapsulated plasmid DNA expressing luciferase is capable of eliciting a systemic antibody response. The N-expressing construct is identical to that expressing luciferase (described in example 3), except for the replacement of the coding sequence with the Edmonston strain MV N coding sequence. The purified plasmid DNA was PLG-encapsulated (using the method as described in example 1).

Figure 6B:
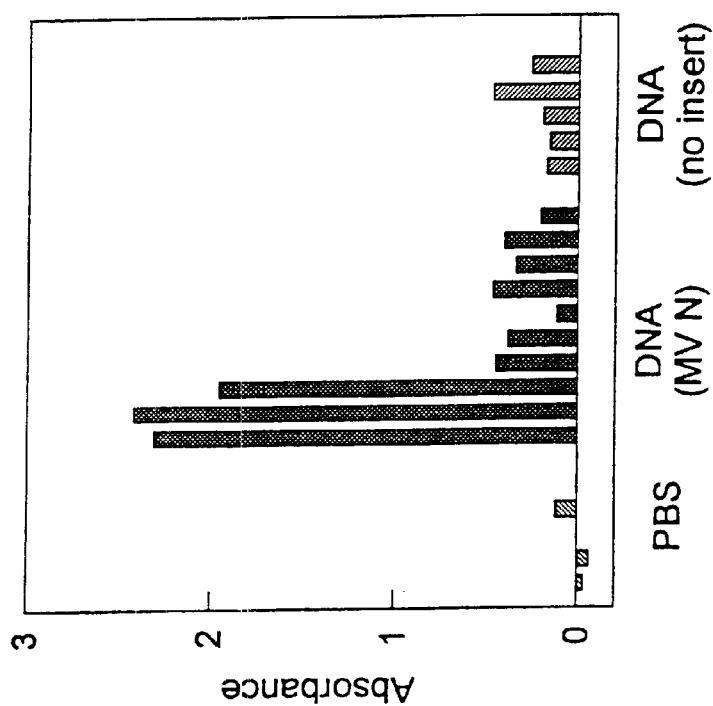
Figure 6A:
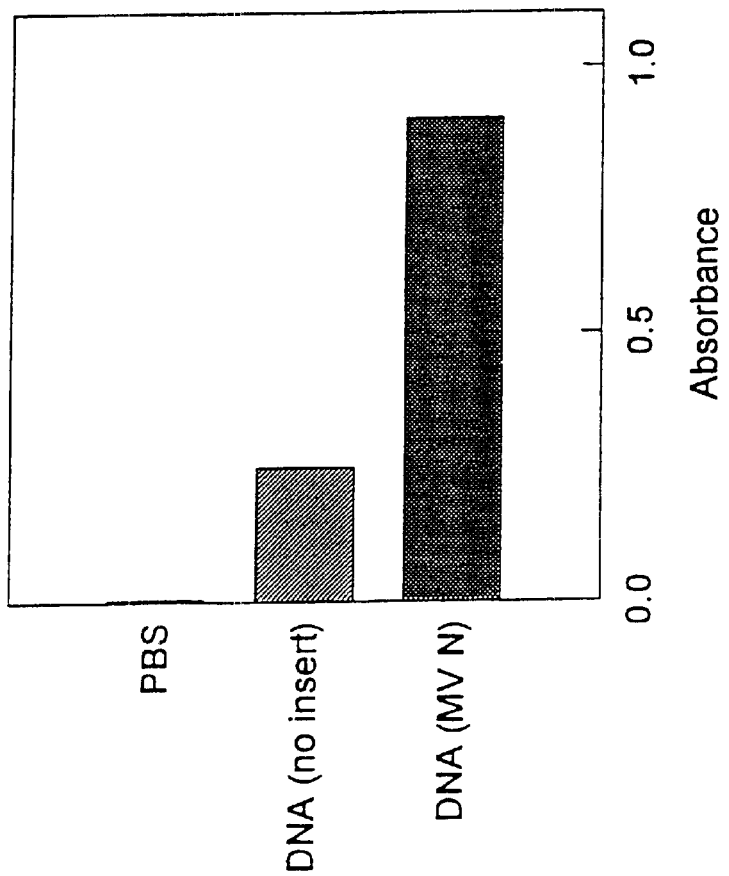
Figure 7B:
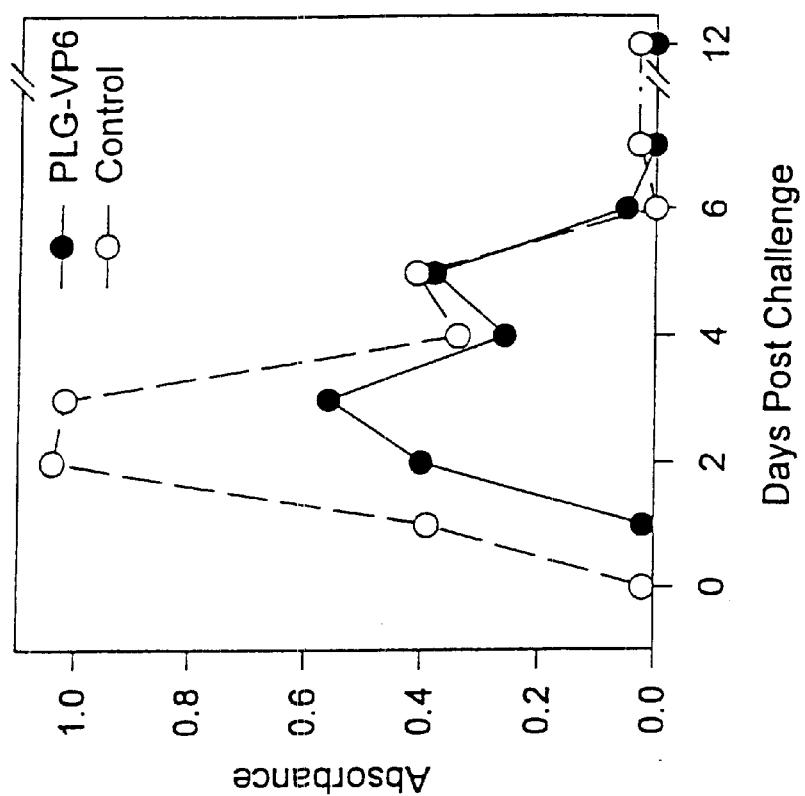
Figure 7A:
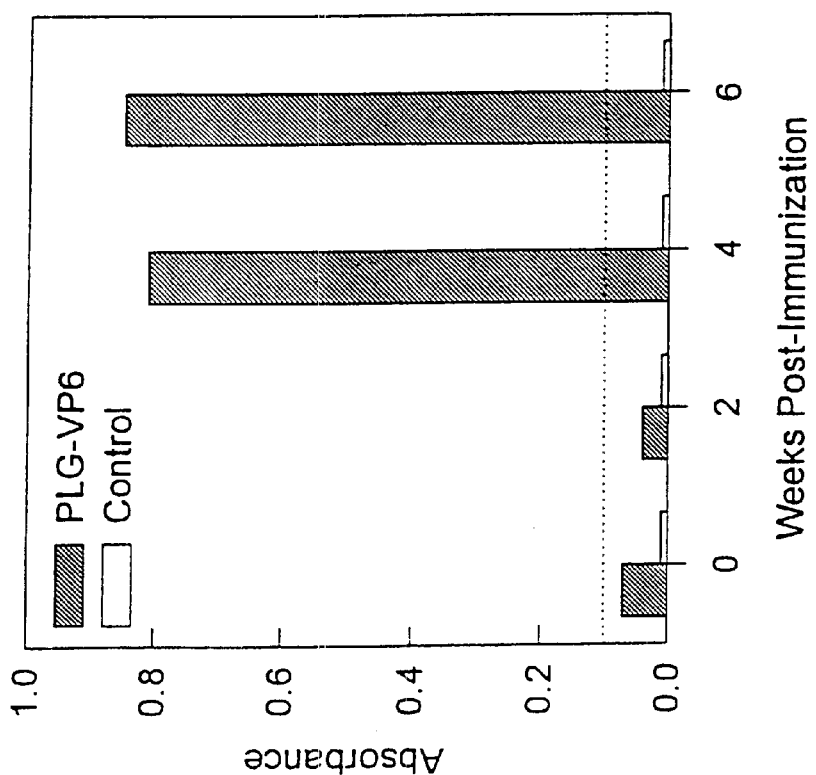

Inbred C3H mice were immunized with two doses suspended in 0.1 M Sodium bicarbonate administered by oral gavage, 13 days apart; each dose contained 50 $\mu$g DNA. Control groups of mice received PBS alone or PLG particles containing plasmid vector DNA containing no coding sequence. Mice were bled at intervals and serum levels of IgG specific for MV N determined by ELISA, using recombinant MV N expressed in insect cells as antigen. As shown in FIG. 6A, immunization with PLG-encapsulated DNA expressing MV N resulted in significant levels of N-specific antibody; results shown are mean absorbances in 1/100 diluted sera taken 53 days after the second DNA administration. There seems to be a considerable degree of variability in the response of individual mice to DNA immunization in these experiments (see FIG. 6B), but very high levels of antibody (reciprocal titres exceeding $10^4$, determined in follow-up experiments) are present in some animals. These results demonstrate that oral delivery of PLG-encapsulated DNA is an effective method for inducing an immune response against an important pathogen.

Example 8

A Further Method for Encapsulation of Plasmid DNA in PLG Microparticles Equipment:

1) Silverson Laboratory mixer with ¾" probe fitted with emulsor screen.
2) High speed centrifuge.
3) Normal laboratory glassware, beakers, measuring cylinders, stirrers etc.

Reagents:

1) Poly(lactide-co-glycolide) (PLG) solution—500 mgs in 3 ml dichloromethane.
2) Plasmid DNA (>10 mg/ml in TE buffer).
3) Polyvinyl alcohol (PVA) solution (8% w/v in water).
4) Absolute ethanol.
5) TE buffer (10 mM tris pH 8.0+1 mM EDTA+50 mM NaCl).

Method:

1) Mix 450 $\mu$l plasmid DNA solution with 150 $\mu$l ethanol with stirring. Mix well.
2) Add this mixture to 3 ml PLG solution and emulsify in the Silverson mixer at 2000 rpm for 2½ min.
3) Add this emulsion to 100 ml PVA and emulsify at 2000 rpm for 2½ min.
4) Add the double emulsion to 1 litre of water and stir vigorously for 1 min.
5) Distribute the suspension of microparticles in centrifuge containers and centrifuge at 10,000×$g_{av}$ for 30 mins.

6) Resuspend the microparticle pellet in 25 ml of water and homogenise with a hand homogeniser with large clearance (0.5 mm) to make a homogeneous suspension. Dilute with 200 ml of water and recentrifuge as above.

7) Repeat steps 5 and 6 four times.

8) Resuspend the microparticle pellet in 25 ml of water as above, transfer to a vessel suitable for freeze drying, shell freeze in an isopropanol/dry ice mixture and lyophilise for 48 h.

In this method, steps 1-3 are carried out at ambient temperature. The efficiency was improved compared to example 1, up to 30-40% efficiency.

Example 9
A Further Method for Encapsulation of Plasmid DNA in PLG Microparticles Equipment:

1) Silverson Laboratory mixer with ¾" probe fitted with emulsor screen.

2) High speed centrifuge.

3) Normal laboratory glassware, beakers, measuring cylinders, stirrers etc.

Reagents:

1) Poly(lactide-co-glycolide) (PLG) solution—400 mgs in 3 ml dichloromethane.

2) Plasmid DNA (>10 mg/ml in TE buffer).

3) Polyvinyl alcohol (PVA) solution (8% w/v in water).

4) Absolute ethanol.

5) TE buffer (10 mM tris pH 8.0+1 mM EDTA.

Method:

1) Mix 450 µl plasmid DNA solution with 150 µl ethanol with stirring. Mix well.

2) Add this mixture to 3 ml PLG solution and emulsify in the Silverson mixer at 2000 rpm for 2½ min.

3) Add this emulsion to 100 ml PVA and emulsify at 2000 rpm for 2½ min.

4) Add the double emulsion to 1 litre of water and stir vigorously for 1 min.

5) Distribute the suspension of microparticles in centrifuge containers and centrifuge at $10,000 \times g_{av}$ for 30 mins.

6) Resuspend the microparticle pellet in 25 ml of water and homogenise with a hand homogeniser with large clearance (0.5 mm) to make a homogeneous suspension. Dilute with 200 ml of water and recentrifuge as above.

7) Repeat steps 5 and 6 four times.

8) Resuspend the microparticle pellet in 25 ml of water as above, transfer to a vessel suitable for freeze drying, shell freeze and lyophilise for 48 h.

In this method, steps 1-3 are carried out at 4° C. The efficiency of incorporation of DNA into microparticles was 50-60%.

Example 10

Plasmid DNA (pCMVIA/VP6) expressing the VP6 gene of murine rotavirus (epizootic diarrhoea of infant mice (EDIM) virus) was constructed at the University of Massachusetts Medical Center. The gene encoding VP6 was inserted into a vector (pJW4303) downstream of sequences of the immediate early transcriptional promoter and intron A of human cytomegalovirus and a tPA-derived secretory signal sequence. The gene was followed by transcriptional termination and polyadenylation sequences derived from the bovine growth hormone gene. The purified plasmid DNA was PLG-encapsulated using the method described in example 1.

Inbred Balb/c mice were immunized by oral administration with a dose containing 50 micrograms VP6-expressing DNA encapsulated in PLG microparticles. A control group of mice received a similar dose of encapsulated vector DNA. Mice were examined for intestinal rotavirus-specific IgA at fortnightly intervals by ELISA, using EDIM virus as antigen. Nine weeks after immunisation, the animals were challenged with EDIM virus, and monitored for excretion of virus in stool using a monoclonal antibody-based ELISA.

As shown in FIG. 7A, immunisation with PLG-encapsulated DNA expressing VP6 resulted in significant levels of rotavirus-specific intestinal IgA antibody when compared with the control animals. This is particularly noteworthy, since other routes of administration of VP6-expressing plasmid DNA do not elicit detectable levels of intestinal virus-specific IgA before virus challenge. After challenge with EDIM virus, there was a reduction in rotavirus shedding in mice which had received PLG-encapsulated VP6-expressing plasmid DNA, compared with the control group (FIG. 7B).

These results demonstrate that orally administered PLG-encapsulated plasmid DNA is capable of inducing a) a specific intestinal IgA response, and b) protection against virus challenge, as manifested in a reduction in virus shedding.

The compositions and methods of the invention have application in slow release systems for delivery of DNA vaccines; prolonged expression of immunogen potentially results in efficient single dose priming and boosting, with consequent efficient induction of long term memory responses. Another application is in a vehicle for the oral delivery of vaccines; simple and acceptable means for vaccine administration are likely to improve vaccine uptake rates; in addition, freeze-dried encapsulated plasmid DNA is likely to be very stable and insensitive to environmental conditions. A further application is in a slow release system for gene therapy; prolonged release of DNA and subsequent expression potentially reduces the need for repeated treatment.

What is claimed is:

1. A synthetic composition comprising a polymer microcapsule and DNA, wherein the DNA (a) is inside the microcapsule, (b) comprises a promoter linked to a sequence coding for an immunogen, and (c) exhibits at least 25% of its pre-encapsulation activity, as assayed by transformation of competent bacteria; and wherein the microcapsule is 10 $\mu$m or less in diameter.

2. The method of claim 1 wherein the DNA is plasmid DNA.

3. The method of claim 1 wherein the DNA comprises a sequence promoting transcription of the sequence coding for the immunogen.

4. The method of claim 1, wherein the composition comprises a plurality of said DNA-containing microcapsules wherein at least 50% of said microcapsules are in the size range 1 $\mu$m to 10 $\mu$m.

5. The method of claim 1, wherein the immunogen induces an immune response that comprises production of antibodies specific to the immunogen.

6. The method of claim 5 wherein the immune response comprises production of IgA antibodies.

7. The method of claim 1, wherein the composition comprises a pharmaceutically acceptable carrier.

8. The method of claim 7 wherein said immunogen is an immunogenic component of an organism selected from the group consisting of a virus and a bacterium.

9. The method of claim 8 wherein the immunogen is a viral protein.

10. The method of claim 1, wherein the polymer has a solubility in methylene chloride of at least 100 mg/ml.

11. The method of claim 1, wherein the microcapsule comprises supercoiled DNA.

12. The method of claim 1 wherein said immunogen elicits a T cell response.

13. The method of claim 12 wherein said T cell response is a cytotoxic T cell (CTL) response.

14. The method of claim 1 wherein said polymer comprises poly(lactide-co-glycolide)(PLG).

15. The method of claim 1, wherein the DNA in said composition retains 50-60% of the pre-encapsulation activity.

16. The method of claim 1, wherein the DNA in said composition retains up to 80% of the pry-encapsulation activity.

17. The method of claim 1, further comprising formulating the composition in the form of a dry powder.

18. The method of claim 1, wherein said polymer consists of PLG.

19. The method of claim 1, where in the polymer is selected from the group consisting of a lactide-containing polymer, a glycolide-containing polymer, and a polymer containing lactide and glycolide.

20. The method of claim 1, wherein the emulsifying speed is below 6000 rpm.

21. The method of claim 1, wherein the emulsifying speed is below 3000 rpm.

22. The method of claim 1, wherein the emulsifying speed is between 1000 and 4000 rpm.

23. A method of administering a composition to a mammal, comprising:
   preparing a composition according to the method of claim 7; and
   administering the composition to a mammal in a manner effective to elicit antibodies against the immunogen.

24. A method of inducing production of an antibody in an animal, comprising:
   preparing a composition according to the method of claim 5; and
   administering to said animal an effective amount of the composition.

25. A method of administering a nucleic acid to an animal, comprising:
   preparing a composition according to the method of claim 1; and
   introducing the composition into the animal.

26. The method of claim 25, wherein the DNA in said composition retains 50-60% of the pre-encapsulation activity.

27. The method of claim 25, wherein the DNA in said composition retains up to 80% of the pre-encapsulation activity.

28. A method of eliciting production of IgA antibodies specific for an immunogen, the method comprising:
   preparing a composition according to the method of claim 1; and
   orally administering the composition to a mammal.

* * * * *

UNITED STATES PATENT AND TRADEMARK OFFICE
CERTIFICATE OF CORRECTION

| | | |
|---|---|---|
| PATENT NO. | : 6,667,294 B2 | Page 1 of 1 |
| APPLICATION NO. | : 08/745515 | |
| DATED | : December 23, 2003 | |
| INVENTOR(S) | : David Hugh Jones, Graham Henry Farrar, and James Christopher Stephen Clegg | |

It is certified that error appears in the above-identified patent and that said Letters Patent is hereby corrected as shown below:

Page 3, left column,
"Jones, D.H., et al.," replace "mcie" with --mice--.
"O'Hagan, D.T." replace the first occurrence of "the" with --The--.

Column 14
Line 45, replace claim 1 with
--1. A method of preparing a composition, the method comprising:
preparing a mixture of DNA and a polymer; and
emulsifying the mixture at an emulsifying speed below 8000 rpm to form a synthetic composition comprising a polymer microcapsule and DNA, wherein the DNA (a) is inside the microcapsule, (b) comprises a sequence coding for an immunogen, and (c) exhibits at least 25% of its pre-encapsulation activity, as assayed by transformation of competent bacteria; and wherein the microcapsule is 10µm or less in diameter.--.

Column 15
Line 26, replace "where in" with --wherein--.

Signed and Sealed this

Twenty-ninth Day of August, 2006

JON W. DUDAS
*Director of the United States Patent and Trademark Office*